US009675527B2

(12) United States Patent
Kita et al.

(10) Patent No.: US 9,675,527 B2
(45) Date of Patent: Jun. 13, 2017

(54) DENTAL COLOR TONE ADJUSTMENT MATERIAL KIT

(71) Applicant: KURARAY NORITAKE DENTAL INC., Kurashiki-shi (JP)

(72) Inventors: Hirotaka Kita, Tainai (JP); Eiichi Terakawa, Tainai (JP); Mizuko Oshita, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 15/033,193

(22) PCT Filed: Oct. 28, 2014

(86) PCT No.: PCT/JP2014/005452
§ 371 (c)(1),
(2) Date: Apr. 29, 2016

(87) PCT Pub. No.: WO2015/064090
PCT Pub. Date: May 7, 2015

(65) Prior Publication Data
US 2016/0250107 A1    Sep. 1, 2016

(30) Foreign Application Priority Data

Oct. 31, 2013 (JP) ................................. 2013-226302

(51) Int. Cl.
| A61K 6/083 | (2006.01) |
| A61K 6/04 | (2006.01) |
| A61K 6/00 | (2006.01) |
| A61K 6/02 | (2006.01) |
| A61C 5/70 | (2017.01) |

(52) U.S. Cl.
CPC .............. *A61K 6/0017* (2013.01); *A61C 5/70* (2017.02); *A61K 6/0002* (2013.01); *A61K 6/0029* (2013.01); *A61K 6/0052* (2013.01); *A61K 6/0055* (2013.01); *A61K 6/0094* (2013.01); *A61K 6/0235* (2013.01); *A61K 6/083* (2013.01)

(58) Field of Classification Search
None
See application file for complete search history.

(56) References Cited

U.S. PATENT DOCUMENTS

| 5,530,038 | A | * | 6/1996 | Yamamoto | ............. | A61K 6/083 |
| | | | | | | 523/116 |
| 6,174,935 | B1 | * | 1/2001 | Matsunae | ............ | A61K 6/0029 |
| | | | | | | 206/63.5 |
| 6,444,725 | B1 | * | 9/2002 | Trom | ................... | A61K 6/0017 |
| | | | | | | 522/25 |
| 6,572,693 | B1 | * | 6/2003 | Wu | ....................... | A61K 6/0017 |
| | | | | | | 106/35 |
| 7,815,434 | B2 | * | 10/2010 | Takei | ................... | A61K 6/0017 |
| | | | | | | 106/35 |
| 8,647,426 | B2 | * | 2/2014 | Craig | ................... | A61K 6/0005 |
| | | | | | | 106/35 |
| 2003/0060533 | A1 | * | 3/2003 | Ohtsuki | ............... | A61K 6/0017 |
| | | | | | | 523/115 |
| 2005/0123880 | A1 | * | 6/2005 | Grundler | ............. | A61C 13/082 |
| | | | | | | 433/215 |
| 2006/0078510 | A1 | * | 4/2006 | Takei | ................... | A61K 6/0017 |
| | | | | | | 424/49 |
| 2009/0047633 | A1 | * | 2/2009 | Huo | ..................... | A61K 6/0017 |
| | | | | | | 433/217.1 |
| 2009/0068123 | A1 | * | 3/2009 | Takei | ..................... | A61K 6/083 |
| | | | | | | 424/52 |

(Continued)

FOREIGN PATENT DOCUMENTS

| JP | 2005-112854 A | 4/2005 |
| WO | 2004/032884 A1 | 4/2004 |
| WO | 2005/087179 A1 | 9/2005 |

OTHER PUBLICATIONS

International Search Report issued Feb. 10, 2015 in PCT/JP2014/005452 filed Oct. 28, 2014.

*Primary Examiner* — Peter A Salamon
(74) *Attorney, Agent, or Firm* — Oblon, McClelland, Maier & Neustadt, L.L.P.

(57) ABSTRACT

The present invention provides a dental color tone adjustment material kit that has improved properties in terms of surface drying and of discoloration after curing and that enables adjustment to a desired color tone. The present invention relates to a dental color tone adjustment material kit including: a primer composition (A) including an acid group-containing polymerizable monomer (a) and a volatile organic solvent (b); and a dental color tone adjustment material B including a polymerizable monomer (d), a polymerization initiator (e), particle aggregates (f) that are chain aggregates of ultrafine filler particles having an average primary particle diameter of 1 to 50 nm, titanium dioxide (g), and a pigment (h). The monomer (a) accounts for 0.05 to 45 weight % of the primer composition (A), and the organic solvent (b) accounts for 55 to 99.95 weight % of the primer composition (A). The monomer (d) includes a polyfunctional acrylate monomer (d1) and a volatile monofunctional (meth)acrylate monomer (d2), and the monomers (d1) and (d2) account for 88 weight % or more of the monomer (d). The content of the particle aggregates (f) is 5 to 20 parts by weight, and the content of the titanium dioxide (g) is 0.05 to 2 parts by weight, per 100 parts by weight of the total of the monomer (d) and the particle aggregates (f).

5 Claims, No Drawings

(56) References Cited

U.S. PATENT DOCUMENTS

| | | | |
|---|---|---|---|
| 2010/0015578 A1* | 1/2010 | Falsafi | A61K 6/0017 433/228.1 |
| 2010/0197824 A1* | 8/2010 | Bissinger | A61K 6/0017 523/116 |
| 2010/0297588 A1* | 11/2010 | Kalgutkar | A61K 6/024 433/228.1 |
| 2011/0003267 A1* | 1/2011 | Terakawa | A61K 6/083 433/228.1 |
| 2011/0053116 A1* | 3/2011 | Hecht | A61K 6/0017 433/199.1 |
| 2011/0200971 A1* | 8/2011 | Kalgutkar | A61K 6/0017 433/201.1 |
| 2011/0257292 A1* | 10/2011 | Okubayashi | A61K 6/0005 523/115 |
| 2013/0137065 A1* | 5/2013 | Velamakanni | A61C 13/09 433/222.1 |
| 2013/0171589 A1* | 7/2013 | Velamakanni | A61O 5/10 433/222.1 |

\* cited by examiner

DENTAL COLOR TONE ADJUSTMENT MATERIAL KIT

TECHNICAL FIELD

The present invention relates to a dental color tone adjustment material kit and particularly relates to a dental color tone adjustment material kit adapted for color tone adjustment of dental restorative materials.

BACKGROUND ART

Recent dental treatment often employs a crown restorative material formed of a sintered zirconia block, glass block, or resin block processed by means of CAD/CAM, in order to repair a lost part of a tooth damaged, for example, by dental caries. Sintered bodies of zirconia are white; thus, a crown restorative material formed of a sintered body of zirconia is inferior to natural teeth in aesthetic quality. Sintered zirconia blocks, glass blocks, and resin blocks can be colored indeed, but adjustment of the color tone of these blocks to a desired one requires the use of many kinds of colorants having different color tones. One possible approach for reproducing the color tone of natural teeth is to use a block having layers of different color tones; however, exact reproduction of the color tone of natural teeth is difficult. Under these circumstances, further studies have been made on methods for adjusting the color tone of the surfaces of the crown restorative materials as mentioned above.

For example, Patent Literature 1 proposes: a method for color correction of replacement teeth or tooth surfaces, the method including application of photocurable corrective colors including: matrix monomers including bisphenol-A-diglycidyl acrylate, urethane dimethacrylate, and triethylene glycol dimethacrylate; a filler mixture of quartz, metal oxides, and dental glass; an initiator; and a slight amount of dental pigments. Patent Literature 1 also proposes a color kit for color correction.

Furthermore, treatment of natural tooth surfaces for maintaining the aesthetic quality of the surfaces has been previously studied.

For example, Patent Literature 2 proposes a dental coating kit that exhibits good bonding to teeth, with the main aim of preventing staining and discoloration of teeth, particularly staining and color return of bleached teeth, the dental coating kit including: a primer composition including an acid group-containing polymerizable monomer (a), water (b), and a water-soluble solvent (c); and a surface smoothing composition including a polyfunctional polymerizable monomer (0, a volatile solvent (g), and a photopolymerization initiator (h).

CITATION LIST

Patent Literature

Patent Literature 1: JP 2005-112854 A
Patent Literature 2: WO 2004/032884 A1

SUMMARY OF INVENTION

Technical Problem

However, the correction colors proposed in Patent Literature 1 have poor surface-curing characteristics, so the surface of a replacement tooth or a natural tooth to which have been applied the correction colors is susceptible to staining with a substance such as coffee and readily undergoes a decrease in gloss even immediately after the application of the correction colors. According to Patent Literature 2 which focuses on making teeth whiter and more beautiful, the color tone of a restored tooth is different from that of natural teeth. Furthermore, Patent Literature 2 is mainly directed to application to teeth, and when a primer and a surface smoothing composition presented as examples in Patent Literature 2 are applied to a surface of a crown restorative material, the surface smoothing composition fails to have satisfactory surface-drying characteristics.

It is therefore an object of the present invention to provide a dental color tone adjustment material kit adapted to show improved surface-drying characteristics of a dental color tone adjustment material, reduce the susceptibility of the cured product of the dental color tone adjustment material to discoloration by a substance such as coffee, exhibit improved abrasion resistance, and allow adjustment to a desired color tone to be made even by applying the material thinly.

Solution to Problem

As a result of a detailed study aimed at achieving the above object, the present inventor has achieved the object by providing a dental color tone adjustment material kit including a primer composition (A) and a dental color tone adjustment material (B), wherein the primer composition (A) includes an acid group-containing polymerizable monomer (a) and a volatile organic solvent (b), the dental color tone adjustment material (B) includes a polymerizable monomer (d), a polymerization initiator (e), particle aggregates (f), titanium dioxide (g), and a pigment (h), a content of the acid group-containing polymerizable monomer (a) is 0.05 to 45 weight % of a total weight of the primer composition (A), a content of the volatile organic solvent (b) is 55 to 99.95 weight % of a total weight of the primer composition (A), the polymerizable monomer (d) includes a polyfunctional acrylate monomer (d1) having three or more acryloyl groups per molecule and a volatile monofunctional (meth)acrylate monomer (d2), a total content of the monomer (d1) and the monomer (d2) is 88 weight % or more of a weight of the polymerizable monomer (d), the particle aggregates (f) are chain aggregates of ultrafine filler particles having an average primary particle diameter of 1 to 50 nm, a content of the particle aggregates (0 is 5 to 20 parts by weight per 100 parts by weight of a total weight of the polymerizable monomer (d) and the particle aggregates (f), a content of the titanium dioxide (g) is 0.05 to 2 parts by weight per 100 parts by weight of a total weight of the polymerizable monomer (d) and the particle aggregates (f), and the pigment (h) is a pigment other than the titanium dioxide (g).

Advantageous Effects of Invention

The present invention can provide a dental color tone adjustment material kit adapted to show good surface-drying characteristics, reduce the susceptibility of a cured product of a dental color tone adjustment material to discoloration by a substance such as coffee, exhibit improved abrasion resistance, and allow adjustment to a desired color tone to be made even by applying the material thinly.

DESCRIPTION OF EMBODIMENTS

The dental color tone adjustment material kit of the present invention includes a primer composition (A) and a dental color tone adjustment material (B). The dental color tone adjustment material kit of the present invention preferably consists of the primer composition (A) and the dental color tone adjustment material (B). The primer composition (A) includes an acid group-containing polymerizable monomer (a) and a volatile organic solvent (b). The content of the acid group-containing polymerizable monomer (a) is 0.05 to 45 weight % of the total weight of the primer composition (A), while the content of the volatile organic solvent (b) is 55 to 99.95 weight % of the total weight of the primer composition (A). The dental color tone adjustment material (B) includes a polymerizable monomer (d), a polymerization initiator (e), particle aggregates (f) that are chain aggregates of ultrafine filler particles having an average primary particle diameter of 1 to 50 nm, titanium dioxide (g), and a pigment (h). The polymerizable monomer (d) includes a polyfunctional acrylate monomer (d1) having three or more acryloyl groups per molecule and a volatile monofunctional (meth) acrylate monomer (d2), the total content of the polyfunctional acrylate monomer (d1) and the volatile monofunctional (meth)acrylate monomer (d2) being 88 weight % or more of the weight of the polymerizable monomer (d). The dental color tone adjustment material (B) contains 5 to 20 parts by weight of the particle aggregates (f) which are chain aggregates of ultrafine filler particles and 0.05 to 2 parts by weight of the titanium dioxide (g), per 100 parts by weight of the total weight of the polymerizable monomer (d) and the particle aggregates (f) which are chain aggregates of ultrafine filler particles.

The components used in the present invention are described in the following paragraphs, in which the primer composition (A) and the dental color tone adjustment material (B) are separately discussed. In the present description, "methacryloyl" and "acryloyl" are collectively referred to as "(meth)acryloyl", and "methacrylate" and "acrylate" are collectively referred to as "(meth)acrylate".

Primer Composition (A)

The primer composition (A) will first be described in detail. The primer composition (A) is intended to be used prior to the use of the dental color tone adjustment material (B). The use of the primer composition (A) improves the bonding between the dental color tone adjustment material (B) and an adherent as exemplified by a tooth or dental restorative material such as a crown restorative material, particularly between the dental color tone adjustment material (B) and a dental restorative material. Consequently, even after a lapse of several days subsequent to the application of the dental color tone adjustment material (B), it remains unlikely that a substance such as coffee enters between the cured product of the dental color tone adjustment material (B) and the adherent and thereby causes discoloration.

Acid Group-Containing Polymerizable Monomer (a)

The acid group-containing polymerizable monomer (a) included in the primer composition (A) has a structure capable of polymerization and forms into a cured product through polymerization. The use of the acid group-containing polymerizable monomer (a) improves the bonding of the primer composition (A) to the surfaces of adherends. An example of the acid group-containing polymerizable monomer (a) is a polymerizable monomer having at least one of acid groups such as a phosphoric acid group, a pyrophosphoric acid group, a thiophosphoric acid group, a phosphonic acid group, a sulfonic acid group, and a carboxylic acid group and further having at least one of polymerizable groups such as an acryloyl group, a methacryloyl group, a vinyl group, and a styrene group. Specific examples of the acid group-containing polymerizable monomer (a) will now be presented.

Examples of the phosphoric acid group-containing polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl] hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl] hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl]hydrogen phosphate; and their acid chlorides, alkali metal salts, and ammonium salts.

Examples of the pyrophosphoric acid group-containing polymerizable monomer include: bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl] pyrophosphate, and bis[10-(meth)acryloyloxydecyl]pyrophosphate; and their acid chlorides, alkali metal salts, and ammonium salts.

Examples of the thiophosphoric acid group-containing polymerizable monomer include: 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, and 20-(meth)acryloyloxyeicosyl dihydrogen thiophosphate; and their acid chlorides, alkali metal salts, and ammonium salts.

Examples of the phosphonic acid group-containing polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate; and their acid chlorides, alkali metal salts, and ammonium salts.

Examples of the sulfonic acid group-containing polymerizable monomer include 2-(meth)acrylamido-2-methylpropanesulfonic acid, styrenesulfonic acid, and 2-sulfoethyl (meth)acrylate.

Examples of the carboxylic acid group-containing polymerizable monomer include a polymerizable monomer having one carboxyl group per molecule and a polymerizable monomer having two or more carboxyl groups per molecule.

Examples of the polymerizable monomer having one carboxyl group per molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and their acid halides.

Examples of the polymerizable monomer having two or more carboxyl groups per molecule include: 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyltrimellitate, 4-(meth)acryloyloxyhexyl trimellitate, 4-(meth)acryloyloxydecyl trimellitate, and 2-(meth)acryloyloxyethyl-3'-(meth)acryloyloxy-2'-(3,4-dicarboxybenzoyloxy)propyl succinate; and their acid anhydrides and acid halides.

Among these acid group-containing polymerizable monomers, the phosphoric or pyrophosphoric acid group-containing (meth)acrylic monomers are preferable since such monomers provide better bonding to adherends. Particularly preferred are the phosphoric acid group-containing (meth)acrylic monomers. Among the phosphoric acid group-containing (meth)acrylic monomers, a divalent phosphoric acid group-containing (meth)acrylic monomer that has as the main chain of the molecule an alkyl or alkylene group having 6 to 20 carbon atoms is more preferable, and a divalent phosphoric acid group-containing (meth)acrylic monomer that has as the main chain of the molecule an alkylene group having 8 to 12 carbon atom is even more preferable. Most preferred is 10-methacryloyloxydecyl dihydrogen phosphate.

One monomer may be contained alone as the acid group-containing polymerizable monomer (a) or a combination of two or more monomers may be contained as the acid group-containing polymerizable monomers (a). Too high or low a content of the acid group-containing polymerizable monomer (a) may result in a decline in bond strength to the surface of an adherend. Too high a content of the acid group-containing polymerizable monomer (a) may cause a large amount of the acid group-containing polymerizable monomer (a) to remain on the adherend, thus resulting in a deterioration in surface-drying characteristics of the dental color tone adjustment material and a reduction in stain resistance or gloss retention of the cured product of the dental color tone adjustment material. Thus, the content of the acid group-containing polymerizable monomer (a) in the primer composition (A) is 0.05 to 45 weight %, preferably 0.05 to 40 weight %, more preferably 0.1 to 20 weight %, and particularly preferably 0.5 to 10 weight %, of the total weight of the primer composition (A).

Volatile Organic Solvent (b)

In the present invention, the volatile organic solvent (b) is an organic solvent that has a boiling point of 120° C. or lower at ordinary pressure and that is liquid at 25° C. Specific examples include methanol, ethanol, 1-propanol, 2-propanol, 1-butanol, 2-methyl-propanol, acetone, methyl ethyl ketone, tetrahydrofuran, diethyl ether, diisopropyl ether, hexane, toluene, chloroform, ethyl acetate, methyl acrylate, methyl methacrylate, and ethyl methacrylate. Among these, ethanol, 2-propanol, 2-methyl-2-propanol, acetone, and methyl methacrylate are preferable in view of safety and volatility. A compound that can be categorized both as the acid group-containing polymerizable monomer (a) and as the volatile organic solvent (b) is regarded herein as an acid group-containing polymerizable monomer (a).

In view of the surface-drying characteristics of the dental color tone adjustment material (B) used in combination with the primer composition (A), the content of the volatile organic solvent (b) is 55 to 99.95 weight %, preferably 75 to 99.9 weight %, more preferably 80 to 99.9 weight %, even more preferably 85 to 99.5 weight %, and particularly preferably 90 to 99.5 weight %, of the total weight of the primer composition (A).

Silane Coupling Agent (C)

The primer composition (A) can further include a silane coupling agent (c). The silane coupling agent (c) undergoes dehydration condensation with silanol groups of an adherend to enhance the bonding between the primer composition (A) and the adherend. Any commonly-known silane coupling agent can be used as the silane coupling agent (c) without limitation. Examples of the silane coupling agent (c) include 3-(meth)acryloyloxypropyltrimethoxysilane, 3-(meth)acryloyloxypropyltriethoxysilane, 3-(meth)acryloyloxypropyltrihexyloxysilane, 6-(meth)acryloyloxyhexyltrimethoxysilane, 6-(meth)acryloyloxyhexyltriethoxysilane, 8-(meth)acryloyloxyoctyltrimethoxysilane, 10-(meth)acryloyloxydecyltrimethoxysilane, 11-(meth)acryloyloxyundecyltrimethoxysilane, 11-(meth)acryloyloxyundecyltriethoxysilane, 11-(meth)acryloyloxyundecyltrihexyloxysilane, 20-(meth)acryloyloxyeicosyltrimethoxysilane, 3-(meth)acryloyloxypropylmethyldimethoxysilane, 3-(meth)acryloyloxypropyldimethylethoxysilane, 11-(meth)acryloyloxyundecylmethyldimethoxysilane, 3-(meth)acryloyloxypropylphenyldimethoxysilane, 3-(meth)acryloyloxypropyltrichlorosilane, 11-(meth)acryloyloxyundecyltrichlorosilane, 3-(meth)acryloyloxypropyldichloromethylsilane, 3-(meth)acryloyloxypropylchlorodimethylsilane, 11-(meth)acryloyloxyundecyldichloromethylsilane, 11-(meth)acryloyloxyundecylchlorodiethylsilane, vinyltrimethoxysilane, vinyltriethoxysilane, vinyltrichlorosilane, vinyltriacetoxysilane, vinyldichloromethylsilane, vinyltri(2-methoxyethoxy)silane, 3-glycidoxypropyltrimethoxysilane, 3-glycidoxypropyltriethoxysilane, 3-aminopropyltrimethoxysilane, allyltriethoxysilane, diallyldichlorosilane, divinyldiethoxysilane, m,p-styrylethyltrimethoxysilane, and 3,4-epoxycyclohexylmethyltrimethoxysilane. In view of the bonding between the primer composition (A) and an adherend and of the handling properties, 3-(meth)acryloyloxypropyltrimethoxysilane, 3-(meth)acryloyloxypropylmethyldimethoxysilane, 3-aminopropyltriethoxysilane, 11-methacryloyloxyundecyltrimethoxysilane, and their hydrolysates are preferable.

One silane coupling agent may be contained alone as the silane coupling agent (c) or a combination of two or more silane coupling agents may be contained as the silane coupling agent (c). When the primer composition (A) includes the silane coupling agent (c), it is preferable, in view of the surface-drying characteristics of the dental color tone adjustment material (B) and the bonding between the primer composition (A) and an adherend, that the primer composition (A) has, for example, the following composition: 0.05 to 40 weight % of the acid group-containing polymerizable monomer (a); 55 to 99.9 weight % of the volatile organic solvent (b); and 0.01 to 40 weight % of the silane coupling agent (c). In particular, the following composition is more preferable: 0.1 to 10 weight % of the acid group-containing polymerizable monomer (a); 80 to 99.8 weight % of the volatile organic solvent (b); and 0.1 to 10 weight % of the silane coupling agent (c). The content of the silane coupling agent (c) may be 0.5 to 10 weight % of the total weight of the primer composition (A).

The primer composition (A) may further include, for example, a polymerizable monomer having no acid group, water, a polymerization initiator, an oxidant, a reductant, or a filler to the extent that the effects of the invention remain unimpaired. Monomers available as the polymerizable monomer having no acid group do not include those which can be categorized as the acid group-containing polymerizable monomer (a), the volatile organic material (b), or the silane coupling agent (c). The primer composition (A) is preferably free of water. This is because, when the primer composition (A) contains water, the water may remain on the surface of the adherend due to insufficient air blowing and deteriorate the surface-drying characteristics of the dental color tone adjustment material, thus causing a reduction in stain resistance and gloss retention.

Dental Color Tone Adjustment Material (B)

The dental color tone adjustment material (B) will next be described in detail. The dental color tone adjustment material (B) is intended to be used subsequent to the use of the primer composition (A). The use of the dental color tone adjustment material (B) in combination with the primer composition (A) provides an improvement in the surface-drying characteristics of the dental color tone adjustment material (B), a reduction in the susceptibility of the cured product of the dental color tone adjustment material to discoloration, and an increase in stain resistance and abrasion resistance.

Polymerizable Monomer (d)

The polymerizable monomer (d) included in the dental color tone adjustment material (B) includes a polyfunctional acrylate monomer (d1) having three or more acryloyl groups per molecule and a volatile monofunctional (meth)acrylate monomer (d2). The total content of the polyfunctional acrylate monomer (d1) and the volatile monofunctional (meth)acrylate monomer (d2) is 88 weight % or more of the total weight of the polymerizable monomer (d). In view of the surface-drying characteristics of the dental color tone adjustment material (B), the total content of the polyfunctional acrylate monomer (d1) and the volatile monofunctional (meth)acrylate monomer (d2) is preferably 94 weight % or more and more preferably 98 weight % or more of the total weight of the polymerizable monomer (d). The polymerizable monomer (d) more preferably consists only of the polyfunctional acrylate monomer (d1) and the volatile monofunctional (meth)acrylate monomer (d2).

Polyfunctional Acrylate Monomer (d1)

The polyfunctional acrylate monomer (d1) has three or more acryloyl groups per molecule. Examples of the polyfunctional acrylate monomer (d1) include trimethylolpropane triacrylate, trimethylolethane triacrylate, tetramethylolmethane triacrylate, pentaerythritol triacrylate, pentaerythritol tetraacrylate, dipentaerythritol hexaacrylate, and 2,2,6,6-tetarakis(acryloyloxymethyl)-4-oxaheptane-1,7-diol 1-acrylate. In particular, in view of handling properties and safety, pentaerythritol triacrylate and dipentaerythritol hexaacrylate are preferable.

One monomer may be contained alone as the polyfunctional acrylate monomer (d1) or a combination of two or more monomers may be contained as the polyfunctional acrylate monomer (d1). The content of the polyfunctional acrylate monomer (d1) is preferably 10 parts by weight to 80 parts by weight per 100 parts by weight of the total of the polyfunctional acrylate monomer (d1) and the volatile monofunctional (meth)acrylate monomer (d2). When the content of the polyfunctional acrylate monomer (d1) is less than 10 parts by weight, the dental color tone adjustment material (B) may have deteriorated surface-drying characteristics, with the result that the cured product of the dental color tone adjustment material may have reduced stain resistance or gloss retention. When the content of the polyfunctional acrylate monomer (d1) is more than 80 parts by weight, the dental color tone adjustment material (B) may have poor handling properties and thus be difficult to apply to the surface of an adherend. The content of the polyfunctional acrylate monomer (d1) is more preferably 30 parts by weight to 75 parts by weight and even more preferably 50 parts by weight to 70 parts by weight per 100 parts by weight of the total of the polyfunctional acrylate monomer (d1) and the volatile monofunctional (meth)acrylate monomer (d2).

Volatile Monofunctional (Meth)Acrylate Monomer (d2)

In the present invention, the volatile monofunctional (meth)acrylate monomer (d2) is a monofunctional (meth)acrylate monomer that has a boiling point of 120° C. or lower at ordinary pressure and that is liquid at 25° C. Examples of the volatile monofunctional (meth)acrylate monomer (d2) include methyl (meth)acrylate and ethyl (meth)acrylate. Methyl methacrylate is most preferable due to its low toxicity and low boiling point.

One monomer may be contained alone as the volatile monofunctional (meth)acrylate monomer (d2) or a combination of two or more monomers may be contained as the volatile monofunctional (meth)acrylate monomer (d2). The content of the volatile monofunctional (meth)acrylate monomer (d2) is preferably 20 parts by weight to 90 parts by weight per 100 parts by weight of the total of the polyfunctional acrylate monomer (d1) and the volatile monofunctional (meth)acrylate monomer (d2). When the content of the volatile monofunctional (meth)acrylate monomer (d2) is less than 20 parts by weight, the dental color tone adjustment material (B) may have poor handling properties and thus be difficult to apply to the surface of an adherend. When the content of the volatile monofunctional (meth)acrylate monomer (d2) is more than 90 parts by weight, the dental color tone adjustment material may have deteriorated surface-drying characteristics, with the result that the cured product of the dental color tone adjustment material may have reduced stain resistance or gloss retention. The content of the volatile monofunctional (meth)acrylate monomer (d2) is more preferably 25 parts by weight to 70 parts by weight and even more preferably 30 parts by weight to 50 parts by weight per 100 parts by weight of the total of the polyfunctional acrylate monomer (d1) and the volatile monofunctional (meth)acrylate monomer (d2).

The polymerizable monomer (d) contained in the dental color tone adjustment material (B) may include a polymerizable monomer (d3) in addition to the polyfunctional acrylate monomer (d1) and the volatile monofunctional (meth)

acrylate monomer (d2). Any commonly-known polymerizable monomer for use in dental compositions can be used as the polymerizable monomer (d3) without limitation. Specific examples of the polymerizable monomer (d3) include: esters of α-cyanoacrylic acid, (meth)acrylic acid, α-halogenated acrylic acid, crotonic acid, cinnamic acid, sorbic acid, maleic acid, and itaconic acid; (meth) acrylamides; (meth)acrylamide derivatives; vinyl esters; vinyl ethers; mono-N-vinyl derivatives; and styrene derivatives. In particular, a (meth)acrylic acid ester or (meth) acrylamide is preferable.

Examples of the (meth)acrylic acid ester and (meth) acrylamide that may be used as the polymerizable monomer will now be presented.

(i) Monofunctional (meth)acrylates and monofunctional (meth)acrylamides The examples include isobutyl (meth) acrylate, benzyl (meth)acrylate, lauryl (meth)acrylate, 2-(N, N-dimethylamino)ethyl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerin mono(meth) acrylate, erythritol mono(meth)acrylate, N-methylol(meth) acrylamide, N-hydroxyethyl(meth)acrylamide, N-(dihydroxyethyl)(meth)acrylamide, (meth)acryloyloxydodecylpyridinium bromide, (meth)acryloyloxydodecylpyridinium chloride, (meth)acryloyloxyhexadecylpyridinium chloride, and (meth)acryloyloxydecylammonium chloride.

(ii) Bifunctional (meth)acrylates and tri- or higher-functional methacrylates The examples include ethylene glycol di(meth)acrylate, triethylene glycol di(meth)acrylate, propylene glycol di(meth)acrylate, neopentyl glycol di(meth) acrylate, 1,6-hexanediol di(meth)acrylate, 1,10-decanediol di(meth)acrylate, bisphenol A diglycidyl (meth)acrylate (or 2,2-bis[4-[3-(meth)acryloyloxy-2-hydroxypropoxy]phenyl] propane, commonly called "Bis-GM"), 2,2-bis[4-(meth) acryloyloxyethoxyphenyl]propane, 1,2-bis[3-(meth)acryloyloxy-2-hydroxypropoxy]ethane, pentaerythritol di(meth) acrylate, [2,2,4-trimethylhexamethylene bis(2-carbamoyloxyethyl)]dimethacrylate, and N,N-(2,2,4-trimethylhexamethylene) bis[2-(aminocarboxy)propane-1, 3-diol]tetramethacrylate.

One monomer may be contained alone as the polymerizable monomer (d3) or a combination of two or more monomers may be contained as the polymerizable monomer (d3). Too high a content of the polymerizable monomer (d3) may lead to deterioration in the surface-drying characteristics of the dental color tone adjustment material (B). The deterioration in the surface-drying characteristics of the dental color tone adjustment material (B) may cause a reduction in the stain resistance or gloss retention of the cured product of the dental color tone adjustment material (B). Thus, it is most preferable for the polymerizable monomer (d) to contain no polymerizable monomer (d3). If the polymerizable monomer (d) contains the polymerizable monomer (d3), the content of the polymerizable monomer (d3) is preferably 12 weight % or less, more preferably 6 weight % or less, and even more preferably 2 weight % or less, of the total weight of the polymerizable monomer (d).

Polymerization Initiator (e)

The polymerization initiator (e) included in the dental color tone adjustment material (B) can be selected from commonly-available polymerization initiators. In particular, polymerization initiators commonly employed in dentistry are preferably used. One initiator for photopolymerization or chemical polymerization may be used alone, or two or more initiators for photopolymerization or chemical polymerization may be used in appropriate combination.

Examples of the photopolymerization initiator include (bis)acylphosphine oxides and α-diketones.

Examples of (bis)acylphosphine oxides that may be used as the photopolymerization initiator include acylphosphine oxides and bisacylphosphine oxides. Examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, and salts thereof. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, and salts thereof.

Preferred among these (bis)acylphosphine oxides are 2,4, 6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of the α-diketones that may be used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is preferable, since it shows maximum absorption at a wavelength in the visible region.

Among the above photopolymerization initiators, at least one selected from the group consisting of 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, 2,4,6-trimethylbenzoylphenylphosphine oxide sodium salt, and camphorquinone is preferably used. The use of at least one of these initiators contributes to obtaining a composition that has excellent photocurability for visible light and near-ultraviolet light and that shows satisfactory photocurability when irradiated with any light source selected from a halogen lamp, a light-emitting diode (LED), and a xenon lamp.

Chemical polymerization initiators that are preferably used as the polymerization initiator (e) include organic peroxides. Organic peroxides that may be used as the chemical polymerization initiator are not particularly limited, and commonly-known organic peroxides can be used. Typical examples of the organic peroxides include ketone peroxides, hydroperoxides, diacyl peroxides, dialkyl peroxides, peroxyketals, peroxyesters, and peroxydicarobnates.

Examples of the ketone peroxides include methyl ethyl ketone peroxide, methyl isobutyl ketone peroxide, methyl-cyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, and t-butyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexine.

Examples of the peroxyketals include 1,1-bis(t-butylperoxy)-3,3,5-trimethylcyclohexane, 1,1-bis(t-butylperoxy)cyclohexane, 2, 2-bis(t-butylperoxy)butane, 2,2-bis(t-butylperoxy)octane, and n-butyl 4,4-bis(t-butylperoxy)valerate.

Examples of the peroxyesters include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleic acid.

Examples of the peroxydicarbonates include di-3-methoxy peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, the diacyl peroxides are preferably used in view of the overall balance of safety, storage stability, and radical formation potential. Among the diacyl peroxides, benzoyl peroxide is more preferably used.

The content of the polymerization initiator (e) is not particularly limited. In view of, for example, the drying characteristics of the resulting dental color tone adjustment material (B), the content of the polymerization initiator (e) is 0.001 to 30 parts by weight per 100 parts by weight of the polymerizable monomer (d). When the content of the polymerization initiator is less than 0.001 parts by weight, sufficient polymerization of the polymerizable monomer (d) may fail to occur, which leads to a decline in the mechanical strength and/or bond strength of the cured product of the dental color tone adjustment material. The content of the polymerization initiator (e) is more preferably 0.05 parts by weight or more and even more preferably 0.10 parts by weight or more per 100 parts by weight of the polymerizable monomer (d). When the content of the polymerization initiator is more than 30 parts by weight, the polymerization initiator may be deposited from the dental color tone adjustment material (B). Thus, the content of the polymerization initiator is more preferably 20 parts by weight or less, even more preferably 15 parts by weight or less, and still even more preferably 10 parts by weight or less.

The dental color tone adjustment material (B) may further contain a polymerization accelerator. Examples of the polymerization accelerator include amines, sulfinic acids, sulfinates, aldehydes, and thiol compounds.

The amines can be classified into aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N,N-dimethylaminoethyl methacrylate, N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, the tertiary aliphatic amines are preferable in view of the drying characteristics and storage stability of the dental color tone adjustment material (B). Among the tertiary aliphatic amines, N, N-dimethylaminoethyl methacrylate, N-methyldiethanolamine, and triethanolamine are more preferably used.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, n-butoxyethyl N, N-dimethylaminobenzoate, 2-(methacryloyloxy)ethyl 4-N,N-dimethylaminobenzoate, 4-N,N-dimethylaminobenzophenone, and butyl 4-dimethylaminobenzoate. Among these, at least one selected from the group consisting of N,N-di(2-hydroxyethyl)-p-toluidine, ethyl 4-(N,N-dimethylamino)benzoate, n-butoxyethyl N, N-dimethylaminobenzoate, and 4-N,N-dimethylaminobenzophenone is preferably used in view of the ability to improve the surface-drying characteristics of the dental color tone adjustment material (B).

Examples of the sulfinic acids and sulfonates include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Preferred are sodium benzenesulfinate, sodium p-toluenesulfinate, and sodium 2,4,6-triisopropylbenzenesulfinate.

Examples of the aldehydes include terephthalaldehyde and benzaldehyde derivatives. Examples of the benzaldehyde derivatives include dimethylbenzaldehyde, p-methyloxybenzaldehyde, p-ethyloxybenzaldehyde, and p-n-octyloxybenzaldehyde. Among these, p-n-octyloxybenzaldehyde is preferably used in view of the ability to improve the surface-drying characteristics of the dental color tone adjustment material (B).

Examples of the thiol compounds include 3-mercaptopropyltrimethoxysilane, 2-mercaptobenzoxazole, decanethiol, and thiobenzoic acid.

The content of the polymerization accelerator is not particularly limited. In view of, for example, the surface-drying characteristics of the dental color tone adjustment material (B), the content of the polymerization accelerator is preferably 0.001 to 30 parts by weight per 100 parts by weight of the polymerizable monomer (d). When the content of the polymerization accelerator is less than 0.001 parts by weight, sufficient polymerization may fail to occur, which leads to a decline in the mechanical strength and/or bond strength of the cured product of the dental color tone adjustment material. The content is more preferably 0.05 parts by weight or more and even more preferably 0.1 parts by weight or more. When the content of the polymerization accelerator is more than 30 parts by weight, the polymerization accelerator may be deposited from the dental color tone adjustment material (B). Thus, the content of the polymerization accelerator is more preferably 20 parts by weight or less and even more preferably 10 parts by weight or less.

Particle Aggregates (f) (Chain Aggregates of Ultrafine Filler Particles)

The particle aggregates (f) (chain aggregates of ultrafine filler particles) contained in the dental color tone adjustment material (B) serve to improve the surface hardness of the dental color tone adjustment material (B) and endow the dental color tone adjustment material (B) with excellent gloss retention. The particle aggregates (f) serve also to impart thixotropy to the dental color tone adjustment material (B) and contribute to adjustment of its viscosity to a level that allows its easy application. The particle aggregates (f) further have the effect of preventing sedimentation of the pigment (h) added together. In view of the surface gloss of the cured product of the dental color tone adjustment material (B), the average primary particle diameter of the ultrafine filler particles constituting the chain aggregates used as the particle aggregates (f) is 1 to 50 nm and more preferably 5 to 50 nm. In the present invention, the average particle diameter of the ultrafine filler particles can be determined by taking a photograph of the particles with a scanning electron microscope (manufactured by Hitachi, Ltd., S-4000) and measuring the particle diameters of (200 or more) particles observed in a unit area of field of view in the photograph by the use of an image-analyzing particle size distribution analysis software (Macview manufactured by Mountech Co., Ltd.). The diameter of each particle is determined as a circle-equivalent diameter corresponding to the diameter of a circle having the same area as the particle. The average primary particle diameter is calculated from the number of particles and their particle diameters. The type and shape of the particle aggregates (f) are not particularly limited. Commonly-known chain aggregates of ultrafine filler particles can be used. Hydrophilic chain aggregates of ultrafine filler particles and hydrophobic chain aggregates of ultrafine filler particles may be used in combination. An ultrafine filler consisting of primary particles monodispersed without aggregation is unfavorable, because the inclusion of such a filler in the dental color tone adjustment material (B) makes no contribution to adjustment of its viscosity and because the inability of such a filler to prevent sedimentation of the pigment is likely to cause defects such as color unevenness.

Examples of the hydrophilic chain aggregates of ultrafine filler particles that are suitable for use include those manufactured by Nippon Aerosil Co., Ltd. under the trade names "AEROSIL (registered trademark) 130", "AEROSIL (registered trademark) 380", "AEROSIL (registered trademark) OX50", "AEROXIDE (registered trademark) Alu C", "AEROXIDE (registered trademark) $TiO_2$ P25", "AEROXIDE (registered trademark) $TiO_2$ P25S", "VP Zirconium Oxide 3-YSZ", and "VP Zirconium Oxide PH".

Examples of the hydrophobic chain aggregates of ultrafine filler particles include those consisting of an intrinsically-hydrophilic filler subjected to surface treatment with, for example, a silane coupling agent. Examples of the silane coupling agent used in surface treatment to prepare hydrophobic chain aggregates of ultrafine filler particles are the same as those mentioned as examples of the silane coupling agent (c) used in the primer composition (A). Examples of hydrophobized chain aggregates of ultrafine filler particles include those manufactured by Nippon Aerosil Co., Ltd. under the trade names "AEROSIL (registered trademark) R972" and "AEROSIL (registered trademark) R974".

A hydrophobic ultrafine filler to be used may be prepared by surface-treating hydrophilic chain aggregates of ultrafine filler particles with, for example, a silane coupling agent. Such surface treatment can be accomplished, for example, by dispersing hydrophilic chain aggregates of ultrafine filler particles in water, adding 3-methacryloyloxypropyltrimethoxysilane to the dispersion, then distilling off the solvent under reduced pressure, and drying the resulting chain aggregates. Examples of the hydrophilic chain aggregates of ultrafine filler particles include those manufactured by Nippon Aerosil Co., Ltd. under the trade names "AEROSIL (registered trademark) Ar380", "AEROSIL (registered trademark) OX50", and "AEROXIDE (registered trademark) Alu C".

The content of the particle aggregates (f) (chain aggregates of ultrafine filler particles) is 5 to 20 parts by weight, preferably 7 to 18 parts by weight, and more preferably 9 to 16 parts by weight per 100 parts by weight of the total of the polymerizable monomer (d) and the particle aggregates (f) (chain aggregates of ultrafine filler particles). Too low a content of the particle aggregates (f) may lead to too low a viscosity and hence to poor handling properties of the dental color tone adjustment material (B) and also cause sedimentation of the pigment and hence color unevenness during storage of the dental color tone adjustment material (B). Too low a content of the particle aggregates (f) may also lead to a decline in the mechanical strength of the dental color tone adjustment material and hence to a reduction in the abrasion resistance of the dental color tone adjustment material applied in an oral cavity. Too high a content of the particle aggregates (f) may lead to too high a viscosity and hence to poor handling properties of the dental color tone adjustment material (B) and also preclude the dental color tone adjustment material from being thinly applied. An increase in the thickness of the dental color tone adjustment material may affect the shape of a dental restorative material prepared in consideration of occlusion and create the need to readjust the shape of the dental restorative material.

In order to have desired handling properties and ability to be applied thinly, the dental color tone adjustment material (B) containing the particle aggregates (f) (chain aggregates of ultrafine filler particles) has a viscosity of preferably 20 to 500 mPa·s, more preferably 20 to 200 mPa·s, even more preferably 20 to 100 mPa·s, particularly preferably 20 to 70 mPa·s, at 23° C. The viscosity of the dental color tone adjustment material (B) can be measured by the method described in "EXAMPLES".

Merely dispersing the particle aggregates (f) (chain aggregates of ultrafine filler particles) in the polymerizable monomer (d) may be insufficient to allow the dental color tone adjustment material (B) to have a preferred viscosity as specified above. In order to allow the dental color tone adjustment material (B) to have a preferred viscosity as specified above, it is preferable that the particle aggregates (f) (chain aggregates of ultrafine filler particles) be subjected to a high shear force and thus crushed to a certain extent while being dispersed in the polymerizable monomer (d) and that the crushed particle aggregates (f) be dispersed in a composition. For example, one possible production method is to first knead the polyfunctional acrylate monomer (d1) and the particle aggregates (f) (chain aggregates of ultrafine filler particles) under a high shear force using a kneader and then mix the kneaded product with a composition having the polymerization initiator (e), the pigment (h), and the titanium dioxide (g) dissolved or dispersed therein. The polyfunctional acrylate monomer (d1) has such a high viscosity that the polyfunctional acrylate monomer (d1) and the particle aggregates (f) (chain aggregates of ultrafine filler particles) are kneaded together under the action of a high shear force. Thus, the particle aggregates (f) (chain aggregates of ultrafine filler particles) are crushed to a certain extent, and the crushed particle aggregates (1) are dispersed in the composition. The length of time of kneading of the polyfunctional acrylate monomer (d1) and the particle aggregates (f) (chain aggregates of ultrafine filler particles) is not particularly limited, and is preferably about 0.1 to 10 hours and more preferably about 1 to 10 hours. The temperature during kneading is not particularly limited. The kneading may be done under heating. The temperature during kneading is preferably about 10 to 90° C. and more preferably about 40 to 90° C. The content of the particle aggregates (f) (chain aggregates of ultrafine filler particles) is preferably 6 to 40 parts by weight, more preferably 7 to 37 parts by weight, and even more preferably 8 to 35 parts by weight per 100 parts by weight of the polyfunctional acrylate monomer (d1). The kneading is followed by mixing with a composition having the polymerization initiator (e), the pigment (h), and the titanium dioxide (g) dissolved or dispersed in the volatile monofunctional (meth)acrylate monomer (d2). This can yield the dental color tone adjustment material (B) having a desired viscosity. If the particle aggregates (f) (chain aggregates of ultrafine filler particles) are added to and kneaded with a polymerizable monomer composition prepared beforehand by mixing of the polyfunctional acrylate monomer (d1) and the volatile monofunctional (meth)acrylate monomer (d2), a high shear force cannot act during kneading because the polymerizable monomer composition does not have a sufficiently-high viscosity due to the low viscosity of the volatile monofunctional (meth)acrylate monomer (d2). This may lead to a failure to crush the particle aggregates (chain aggregates of ultrafine filler particles) during dispersing and consequently cause the resulting composition to have a viscosity of 5000 mPa·s or more. The dental color tone adjustment material (B) undergoes no sedimentation of the pigment despite having a low viscosity of 20 to 100 mPa·s at 23° C. This leads to the inference that the particle aggregates (f) (chain aggregates of ultrafine filler particles) are present in the dental color tone adjustment material (B) without having been crushed completely into primary particles. If a composition is formed in the same manner as the dental color tone adjustment material (B) except that the particle aggregates (f) (chain aggregates of ultrafine filler particles) are replaced by ultrafine filler particles that can be monodispersed in the form of primary particles without aggregation, the composition may indeed have a viscosity of 20 to 100 mPa·s at 23° C. but will be likely to suffer sedimentation of the pigment.

Titanium Dioxide (g)

The titanium dioxide (g) included in the dental color tone adjustment material (B) scatters light and thus makes the dental color tone adjustment material (B) look white. The titanium dioxide (g) has high hiding power. Thus, the color of an adherend can be corrected even by thinly applying the dental color tone adjustment material (B) including the titanium dioxide (g), and the variation in color depending on the thickness of the applied material (B) is small. Adjusting the content of the titanium dioxide (g) to an appropriate level allows a dental restorative material to keep the transparency close to that of natural teeth. Too low a content of the titanium dioxide (g) may cause insufficient hiding power, which makes difficult the color tone adjustment of a dental restorative material, and may lead to deepening of color tone associated with increasing thickness of the applied material (B) and hence to high occurrence of unevenness of the applied color. Too high a content of the titanium dioxide (g) may give rise to an excessive increase in opacity of the dental color tone adjustment material (B) and hence to a decline in aesthetic quality, and may also lead to a deterioration in surface-drying characteristics of the dental color tone adjustment material (B) and hence to an increase in susceptibility to staining or a reduction in gloss retention. The content of the titanium dioxide (g) is 0.05 to 2 parts by weight, preferably 0.1 to 1.5 parts by weight, and more preferably 0.3 to 1 parts by weight per 100 parts by weight of the total of the polymerizable monomer (d) and the particle aggregates (f) (chain aggregates of ultrafine filler particles).

The average diameter of particles of the titanium dioxide (g) is not limited. The average particle diameter is preferably 0.1 to 10 μm in view of, for example, the gloss of the dental color tone adjustment material (B). The average particle diameter less than 0.1 μm may lead to a failure to achieve satisfactory color production. The average particle diameter more than 10 μm may cause an increase in the susceptibility of the titanium dioxide to sedimentation. The average particle diameter of the titanium dioxide (g) is more preferably 0.2 μm or more and 5 μm or less, and even more preferably 1 μm or less. The method for measuring the average particle diameter of the titanium dioxide (g) may be the same as that for measuring the average particle diameter of the ultrafine filler particles previously described.

Pigment (h)

The pigment (h) used in the dental color tone adjustment material (B) refers to a pigment other than the titanium dioxide (g). Any commonly-known pigment can be used as the pigment (h) without limitation. Pigments are broadly classified into inorganic pigments and organic pigments. An inorganic pigment and an organic pigment may be used in combination. Examples of the inorganic pigment include oxides, hydroxides, sulfides, chromates, silicates, sulfates, carbonates, ferrocyanide compounds, phosphates, and carbon. Among these, oxides are suitable for use. Specific examples of the oxides include red iron oxide, yellow iron oxide, and black iron oxide. The red iron oxide refers to colcothar or hematite, which is iron oxide represented by the chemical formula $Fe_2O_3$. The yellow iron oxide refers to goethite, which is iron oxide represented by the chemical formula FeOOH. The black iron oxide refers to magnetite, which is iron oxide represented by the chemical formula $Fe_3O_4$.

Examples of the organic pigment include azo pigments, phthalocyanine pigments, condensed polycyclic pigments, nitro pigments, nitroso pigments, and fluorescent pigments. Among these, azo pigments and phthalocyanine pigments are suitable for use. Specific examples of the azo pigments include Novoperm Yellow 4G, Cromophtal Yellow 3G, Cromophtal Yellow 3RLP, Novoperm Red BN, Cromophtal Scarlet RN, Cromophtal Blue 4GNP, and Blue No. 2 aluminum lake. Specific examples of the phthalocyanine pigments include phthalocyanine blue and phthalocyanine green.

The content of the pigment (h) is not limited. In view of, for example, the surface-drying characteristics of the dental color tone adjustment material (B), the content of the pigment (h) is, for example, 0.001 to 30 parts by weight per 100 parts by weight of the total of the polymerizable monomer (d) and the particle aggregates (f) (chain aggregates of ultrafine filler particles). The content of the pigment which is less than 0.001 parts by weight may lead to a failure to achieve satisfactory color impartation. The content of the pigment which is more than 30 parts by weight may give rise to poor drying characteristics of the dental color tone adjustment material (B). The content of the pigment (h) is preferably 0.01 parts by weight or more and 20 parts by weight or less, more preferably 10 parts by weight or less, even more preferably 5 parts by weight or less, per 100 parts by weight of the total of the polymerizable monomer (d) and the particle aggregates (f) (chain aggregates of ultrafine filler particles).

The average diameter of particles of the pigment (h) is not limited. In view of, for example, the gloss of the dental color tone adjustment material (B), the average particle diameter is preferably 0.1 to 10 µm. The average particle diameter of the pigment which is less than 0.1 µm may lead to a failure to achieve satisfactory color production. The average particle diameter of the pigment which is more than 10 µm may give rise to an increase in the susceptibility of the pigment to sedimentation. The average particle diameter of the pigment (h) is more preferably 0.2 µm or more and 5 µm or less, particularly preferably 1 µm or less. The method for measuring the average particle diameter of the pigment (h) may be the same as that used for measuring the average particle diameter of the ultrafine filler particles previously described.

Thanks to the inclusion of both the titanium dioxide (g) and the pigment (h) in the dental color tone adjustment material (B), the adjustment of the color tone of the cured product of the dental color tone adjustment material (B) is easy, and adjustment to a color tone close to that of natural teeth is possible. Furthermore, a difference in color tone is less likely to occur between the dental color tone adjustment material that has yet to be cured and the cured product of the dental color tone adjustment material. Additionally, adjustment to a desired color tone, such as a color tone close to that of natural teeth, is possible even by applying the dental color tone adjustment material (B) thinly, and color variation depending on the thickness of the applied material (B) is small. These effects can be reliably achieved when the contents of both the titanium dioxide (g) and the pigment (h) are in the preferred ranges specified above.

The dental color tone adjustment material (B) may additionally contain, for example, an ultraviolet absorber, an antioxidant, a polymerization inhibitor, an X-ray contrast agent, a thickener, or a fluorescent agent to the extent that the effects of the invention remain unimpaired.

When, for example, the cured product of the dental color tone adjustment material (B) is desired to release fluorine ions from its surface, the dental color tone adjustment material (B) can additionally contain a fluorine ion-releasing filler such as fluoroaluminosilicate glass, calcium fluoride, sodium fluoride, or sodium monofluorophosphate.

The dental color tone adjustment material kit of the present invention is suitable for use in color tone adjustment of dental restorative materials such as an inlay, an onlay, and a crown which are fabricated from an organic or inorganic material for dental restoration, from porcelain, from ceramic, or from a sintered zirconia block, glass block, or resin block processed by means of CAD/CAM. In another aspect, the present invention provides a color tone adjustment material kit for dental restorative materials that includes the dental color tone adjustment material kit of the present invention.

The present invention encompasses embodiments obtainable by combining the above features in various manners within the technical scope of the present invention as long as such embodiments exert the effects of the present invention.

EXAMPLES

The present invention will now be described in more detail by way of Examples. It should be noted that the present invention is not limited to Examples given below. The test methods and materials used in Examples will be collectively described later.

Abbreviations used hereinafter are as follows.
[Acid Group-Containing Polymerizable Monomer (a)]
MDP: 10-methacryloyloxydecyl dihydrogen phosphate
M12P: 12-methacryloyloxydodecyl dihydrogen phosphate
[Volatile Organic Solvent (b)]
EtOH: Ethanol
MMA: Methyl methacrylate
[Silane Coupling Agent (c)]
KBM 503: 3-methacryloyloxypropyltrimethoxysilane
KBE 903: 3-aminopropyltriethoxysilane
11-MUS: 11-methacryloyloxyundecyltrimethoxysilane
[Polyfunctional Acrylate Monomer (d1)]
DPE-6A: Dipentaerythritol hexaacrylate
PE-3A: Pentaerythritol triacrylate
[Volatile Monofunctional (Meth)Acrylate Monomer (d2)]
MMA: Methyl methacrylate
EMA: Ethyl methacrylate
[Polymerizable Monomer (d3) Other than (d1) and (d2)]
UDMA: [2,2,4-trimethylhexamethylene-bis(2-carbamoyloxyethyl)]dimethacrylate
U-4TH: N,N-(2,2,4-trimethylhexamethylene)bis[2-(aminocarboxy)propane-1,3-diol]tetramethacrylate
3G: Triethylene glycol dimethacrylate
[Polymerization Initiator (e)]
TMDPO: 2,4,6-trimethylbenzoyldiphenylphosphine oxide
CQ: dl-camphorquinone
Amine: Ethyl 4-(N,N-dimethylamino)benzoate
[Particle Aggregates (f) (Chain Aggregates of Ultrafine Filler Particles)]
R972: "R972" manufactured by Nippon Aerosil Co., Ltd., Average primary particle diameter=16 nm
Silane-Treated Ar380
AEROSIL (registered trademark) Ar380 manufactured by Nippon Aerosil Co., Ltd. (average primary particle diameter=7 nm) was dispersed in 500 mL of water to prepare a dispersion, to which was added 8 g of 3-methacryloyloxypropyltrimethoxysilane and which was then stirred at room temperature for 2 hours. This was followed by distillation under reduced pressure for solvent removal and then by drying at 90° C. for 3 hours. Thus, silane-treated Ar380 was obtained.
Silane-Treated OX50
AEROSIL (registered trademark) OX50 manufactured by Nippon Aerosil Co., Ltd. (average primary particle diameter=40 nm) was dispersed in 500 mL of water to prepare a dispersion, to which was added 8 g of 3-methacryloyloxypropyltrimethoxysilane and which was then stirred at room temperature for 2 hours. This was followed by distillation under reduced pressure for solvent removal and then by drying at 90° C. for 3 hours. Thus, silane-treated OX50 was obtained.

Silane-Treated AL-C

AEROXIDE (registered trademark) Alu C manufactured by Nippon Aerosil Co., Ltd. (average primary particle diameter=20 nm) was dispersed in 500 mL of water to prepare a dispersion, to which was added 15 g of 3-methacryloyloxypropyltrimethoxysilane and which was then stirred at room temperature for 2 hours. This was followed by distillation under reduced pressure for solvent removal and then by drying at 90° C. for 3 hours. Thus, silane-treated AL-C was obtained.

[Other Fillers]

Silane-Treated NF180

An amount of 200 g of barium boroaluminosilicate glass powder (GM27884, NF180, manufactured by SCHOTT AG and having an average primary particle diameter of 0.18 μm) was dispersed in 500 mL of water to prepare a dispersion, to which was added 8 g of 3-methacryloyloxypropyltrimethoxysilane and which was then stirred at room temperature for 2 hours. This was followed by distillation under reduced pressure for solvent removal and then by drying at 90° C. for 3 hours for surface treatment. Thus, silane-treated NF180 was obtained.

Silane-Treated Ultrafine Filler Monodisperse Particles

An aqueous monodisperse silica-alumina sol (Cataloid-SN, manufactured by JGC Catalysts and Chemicals Ltd., having an average primary particle diameter of 12 nm and a silica-alumina content of 20 weight %) was subjected to solvent replacement in which the water was replaced by methanol, and thus a methanol monodisperse sol having a solids content of 20 weight % was obtained. This sol and ethanol were mixed. To the mixed liquid was then added 3-methacryloyloxypropyltrimethoxysilane to obtain a monodisperse sol of silica-alumina particles having surfaces modified with 3-methacryloyloxypropyltrimethoxysilane. Next, the solvent of the resulting monodisperse sol was replaced by methyl methacrylate to obtain a methyl methacrylate monodisperse sol of silica-alumina particles having surfaces modified with 3-methacryloyloxypropyltrimethoxysilane.

[Titanium Dioxide (g)]

Titanium dioxide: Pigment White 6, Average particle diameter=0.2 μm

[Pigment (h)]

Yellow pigment: Novoperm Yellow 4G, Average particle diameter=0.2 μm

Red pigment: Novoperm Red BN, Average particle diameter=0.2 μm

Black pigment: Iron black, Average particle diameter=0.2 μm

Example 1

An amount of 3 g (3 parts by weight) of MDP and 97 g (97 parts by weight) of ethanol were mixed to obtain 100 g of a homogeneous liquid composition. This composition was defined as a primer composition 1.

An amount of 50 g (50 parts by weight) of DPE-6A and 10 g (10 parts by weight) of R972 were kneaded using a mixer/stirrer (Twinmix manufactured by DALTON CO., LTD.) at 50° C. for 3 hours to give 60 g of a paste composition. In a 50 ml capped glass container (screw cap bottle, manufactured by AS ONE Corporation) was put 4 g (40 parts by weight) of MMA, to which were added 0.3 g (3 parts by weight) of TMDPO, 0.009 g (0.09 parts by weight) of the yellow pigment, 0.001 g (0.01 parts by weight) of the red pigment, 0.01 g (0.1 parts by weight) of the black pigment, and 0.06 g (0.6 parts by weight) of the titanium dioxide. The mixture was processed by an ultrasonic cleaner in an ice bath for 1 hour to obtain a liquid composition. Into this liquid composition was introduced 6 g of the previously-obtained paste composition. The compositions were mixed using a mix rotor (manufactured by AS ONE Corporation) overnight to obtain a dental color tone adjustment composition 1.

The combined use of the primer composition 1 and the dental color tone adjustment composition 1 prepared as above was subjected to tests for surface-drying characteristics, tensile bond strength, coffee staining, and abrasion resistance according to the methods described later. The results are shown in Table 1.

Examples 2 to 17 and Comparative Examples 1 to 6

Primer compositions 2 to 23 were prepared in the same manner as in Example 1, except for using the weight ratios shown in Table 1 and Table 2. The combined use of each of these primer compositions and the dental color tone adjustment composition 1 prepared in Example 1 was subjected to tests for surface-drying characteristics, tensile bond strength, coffee staining, and abrasion resistance according to the methods described later. The results are shown in Table 1 and Table 2.

Examples 18 to 32 and Comparative Examples 7 to 14

Dental color tone adjustment compositions were prepared in the same manner as in Example 1, except for using the weight ratios shown in Table 3. The combined use of the primer composition 1 obtained in Example 1 and each of these dental color tone adjustment compositions was subjected to tests for surface-drying characteristics, coffee staining, abrasion resistance, gloss retention, and viscosity according to the methods described later. The results are shown in Table 3 and Table 4.

Comparative Example 15

In a 50 ml capped glass container (screw cap bottle, manufactured by AS ONE Corporation) was put 5 g of the above-prepared methyl methacrylate monodisperse sol of silica-alumina particles (containing 40 parts by weight of MMA and 10 parts by weight of ultrafine filler monodisperse particles), to which were added 0.3 g (3 parts by weight) of TMDPO, 0.009 g (0.09 parts by weight) of the yellow pigment, 0.001 g (0.01 parts by weight) of the red pigment, 0.01 g (0.1 parts by weight) of the black pigment, and 0.06 g (0.6 parts by weight) of the titanium dioxide. The mixture was processed by an ultrasonic cleaner in an ice bath for 1 hour to obtain a liquid composition. Into the liquid composition was introduced 5 g (50 parts by weight) of DPE-6A. The composition and DPE-6A were mixed using a mix rotor (manufactured by AS ONE Corporation) overnight to obtain a dental color tone adjustment composition 22.

The combined use of the primer composition 1 obtained in Example 1 and the dental color tone adjustment composition 22 prepared as above was subjected to tests for surface-drying characteristics, coffee staining, abrasion resistance, gloss retention, and viscosity according to the methods described later. The results are shown in Table 4.

Examples 33 to 35 and Comparative Examples 16 to 18

The combined use of the primer composition 1 and each of the dental color tone adjustment compositions 1, 6, 7, 21, 23, and 20 was subjected to a measurement according to a method for testing color imparting properties. The results are shown in Table 5.

Example 36

The primer composition 1 was applied to "Vita classical" A2 shade guide subjected to sandblasting, and was dried by blowing air over the surface of the applied primer until the primer lost its flowability. Subsequently, the dental color tone adjustment composition 1 was applied once with a flat brush (the thickness of the applied composition=about 20 µm) and irradiated with light for 90 seconds using an irradiator for dental technology, α-light III (manufactured by Morita Corporation). The resulting sample was visually compared with "VITA classical" A3 shade guide and was found to have the same color tone as "VITA classical" A3 shade guide.

Example 37

The same procedures as in Example 36 were performed, except that the dental color tone adjustment composition 1 was applied twice with a flat brush (the thickness of the applied composition=about 40 µm). The resulting sample was visually compared with "VITA classical" A3.5 shade guide and was found to have the same color tone as "VITA classical" A3.5 shade guide.

Example 38

A dental color tone adjustment composition 24 was prepared by performing the same procedures as in Example 1, except for using 0.011 g (0.11 parts by weight) of the yellow pigment, 0.002 g (0.02 parts by weight) of the red pigment, and 0.01 g (0.1 parts by weight) of the black pigment. The same procedures as in Example 36 were then performed, except for using the dental color tone adjustment composition 24. The resulting sample was visually compared with "VITA classical" B2 shade guide and was found to have the same color tone as "VITA classical" B2 shade guide.

Example 39

The same procedures as in Example 38 were performed, except that the dental color tone adjustment composition 24 was applied twice with a flat brush (the thickness of the applied composition=about 40 µm). The resulting sample was visually compared with "VITA classical" B3 shade guide and was found to have the same color tone as "VITA classical" B3 shade guide.

Example 40

A dental color tone adjustment composition 25 was prepared by performing the same procedures as in Example 1, except for using 0.05 g (0.5 parts by weight) of the titanium dioxide, 0.006 g (0.06 parts by weight) of the yellow pigment, 0.001 g (0.01 parts by weight) of the red pigment, and 0.24 g (0.24 parts by weight) of the black pigment. The same procedures as in Example 36 were then performed, except for using the dental color tone adjustment composition 25. The resulting sample was visually compared with "VITA classical" C2 shade guide and was found to have the same color tone as "VITA classical" C2 shade guide.

Example 41

The same procedures as in Example 40 were performed, except that the dental color tone adjustment composition 25 was applied twice with a flat brush (the thickness of the applied composition=about 40 µm). The resulting sample was visually compared with "VITA classical" C3 shade guide and was found to have the same color tone as "VITA classical" C3 shade guide.

Comparative Example 19

The same procedures as in Example 36 were performed, except that the dental color tone adjustment composition 20 was applied once with a flat brush (the thickness of the applied composition=about 20 µm). The resulting sample was visually compared with "VITA classical" A2 shade guide and was found to have become whitish and failed to attain a desired color tone.

Comparative Example 20

The same procedures as in Example 36 were performed, except that the dental color tone adjustment composition 21 was applied once with a flat brush (the thickness of the applied composition=about 20 µm). The resulting sample was visually compared with "VITA classical" A2 shade guide and was found to have undergone no change in color tone and failed to attain a desired color tone.

[Test for Surface-Drying Characteristics]

Each of the primer compositions of Examples and Comparative Examples was applied to "VITA classical" shade guide subjected to sandblasting, and was dried by blowing air over the surface of the applied primer until the primer lost its flowability. Subsequently, each of the dental color tone adjustment compositions of Examples and Comparative Examples was applied and irradiated with light for 90 seconds using an irradiator for dental technology, α-light III (manufactured by Morita Corporation). The color tone adjustment material was vigorously rubbed with a waste cloth (JK wiper 150-S, manufactured by Jujo Kimberly K.K.), and it was visually determined whether or not the monomer remaining unpolymerized and bruises were present. Color tone adjustment materials free of bruises were determined to have a dried surface and rated as "Good". Those found to have a small number of bruises were rated as "Average", and those with many bruises were determined to have failed in surface drying and rated as "Poor".

[Test for Tensile Bond Strength]

A hard resin for tooth crowns, ESTENIA C&B (E4, manufactured by Kuraray Noritake Dental Inc.) was used as an adherend, and formed into a cured sheet having dimensions of 10×10×2 mm by polymerization according to the instructions provided by the manufacturer. A stainless steel sheet having dimensions of 12×12×2 mm was lined with the cured sheet via PANAVIA 21 (manufactured by Kuraray Noritake Dental Inc.). The surface of the resin was ground with #3000 waterproof abrasive paper and then buffed with 3-µm diamond paste into a mirror-polished surface. This was followed by washing with an ultrasonic cleaner, by washing with running water, and then by air blowing for drying. A 5-mm-diameter hole was formed in a 0.13-mm-thick tape to prepare an area-defining tape. This tape was attached to the surface of the resin to define an adhesive area having a diameter of 5 mm. Each of the primer compositions of Examples and Comparative Examples was applied to such a defined area, and was dried by blowing air over the surface of the applied primer until the primer lost its flowability. Subsequently, each of the dental color tone adjustment compositions of Examples and Comparative Examples was applied and then polymerized by irradiating the composition with light for 90 seconds using an irradiator for dental technology, α-light III (manufactured by Morita Corporation). The surface having undergone polymerization was lightly sandblasted and washed. A sandblasted stainless steel rod was then implanted on the surface with the help of PANAVIA 21. In this manner, five test specimens were prepared. Each test specimen was kept immersed in 37° C. water for 24 hours, after which the specimen was subjected to measurement by a universal testing machine (Autograph AG-100 kNl) with the crosshead speed set at 2 mm/minute. The strength value obtained in the test was divided by the adhesive area, and the resulting value was defined as the bond strength of the test specimen. An average of the measured values of the five test specimens was employed as the index of the bond strength. The bond strength is preferably 5 MPa or more, more preferably 7 MPa or more, and most preferably 10 MPa or more.

[Test for Coffee Staining]

A mold having dimensions of 15 mm (diameter)×1 mm was filled with a hard resin for tooth crowns, ESTENIA C&B (E4, manufactured by Kuraray Noritake Dental Inc.), which was polymerized into a cured sheet by irradiating it with light for 180 seconds using an irradiator for dental technology, α-light III (manufactured by Morita Corporation). The surface of the cured sheet was ground with #3000 waterproof abrasive paper and then buffed with 3-μm diamond paste into a mirror-polished surface. Each of the primer compositions of Examples and Comparative Examples was applied to the surface of such a cured sheet and was dried by blowing air over the surface of the applied primer until the primer lost its flowability. Next, a spacer having a thickness of 100 μm, an outer diameter of 15 mm, and an inner diameter of 10 mm was attached to the primer. Each of the dental color tone adjustment composition of Examples and Comparative Examples was put in the hole of such a spacer. An excess of the dental color tone adjustment composition was removed with a razor blade to flatten the surface of the composition, which was then polymerized by irradiating it with light for 90 seconds using an irradiator for dental technology, α-light III (manufactured by Morita Corporation). The color tone of the test specimen that had yet to be treated as below was measured using a color-difference meter ("SE 6000" manufactured by NIPPON DENSHOKU INDUSTRIES CO., LTD.) and using illuminant D65/2 as a light source.

The test specimen was immersed in 99.5 wt % ethanol at room temperature for 24 hr, subsequently further immersed in a 2 wt % aqueous coffee solution and stored at 37° C. for 3 days. The test specimen was then taken out, briefly washed with running water, and dried with gentle air blowing. The color tone of the test specimen thus treated was measured using the color difference meter.

The difference in color tone (ΔE*) before and after the treatment was determined and employed as an index of coffee staining. The chromatic parameters measured before the treatment were expressed as $L^*_1$, $a^*_1$, and $b^*_1$. The chromatic parameters measured after the treatment were expressed as $L^*_2$, $a^*_2$, and $b^*_2$. The color difference (ΔE*) was calculated according to the equation given below. The ΔE* is preferably 6 or less and more preferably 5 or less.

$$\Delta E^* = ((L^*_1 - L^*_2)^2 + (a^*_1 - a^*_2)^2 + (b^*_1 - b^*_2)^2)^{0.5}$$

[Test for Abrasion Resistance]

A mold having a width of 20 mm, a length of 30 mm, and a thickness of 2 mm was filled with a hard resin for tooth crowns, ESTENIA C&S (E4, manufactured by Kuraray Noritake Dental Inc.), and both sides of the resin were each irradiated with light for 180 seconds using an irradiator for dental technology, "α-light III", to obtain a cured product of the resin. The surface of the cured product was ground with #3000 waterproof abrasive paper and then buffed with 3-μm diamond paste into a mirror-polished surface. A 10-mm-square area in the center of the polished surface was roughened by means of carborundum. Each of the primer compositions of Examples and Comparative Examples was applied to such a roughened surface, and was dried by blowing air over the surface of the applied primer until the primer lost its flowability. Subsequently, each of the dental color tone adjustment compositions of Examples and Comparative Examples was applied and polymerized by irradiating it with light for 180 seconds using an irradiator for dental technology, α-light III (manufactured by Morita Corporation). The color tone of the central area (the surface to which the composition was applied) of the test specimen that had yet to be treated as below was measured using a color-difference meter ("SE 6000" manufactured by NIPPON DENSHOKU INDUSTRIES CO., LTD.) and using illuminant D65/2 as a light source.

Afterwards, a slurry containing 40 weight % of a toothpaste (manufactured by Lion Corporation under the trade name "White & White") and 60 weight % of distilled water was prepared. Bristles of a toothbrush (manufactured by Lion Corporation under the trade name "Between", Hardness of bristles: Regular) were brought into direct contact with the surface of the outermost layer of the specimen placed in the slurry, and the toothbrush was slid back and forth 40,000 times with an amplitude of 10 cm under a load of 250 g. Then, the color tone of the central area (the surface to which the composition was applied) of the test specimen thus treated was measured.

The chromatic parameters measured before the treatment were expressed as $L^*_1$, $a^*_1$, and $b^*_1$. The chromatic parameters measured after the treatment were expressed as $L^*_2$, $a^*_2$, and $b^*_2$. The color difference (ΔE*) was calculated according to the equation given below. The ΔE* is preferably 6 or less and more preferably 5 or less.

$$\Delta E^* = ((L^*_1 - L^*_2)^2 + (a^*_1 - a^*_2)^2 + (b^*_1 - b^*_2)^2)^{0.5}$$

[Gloss Retention]

A mold having a width of 20 mm, a length of 30 mm, and a thickness of 2 mm was filled with a hard resin for tooth crowns, ESTENIA C&B (E4, manufactured by Kuraray Noritake Dental Inc.), and the both sides of the resin were each irradiated with light for 180 seconds using an irradiator for dental technology, α-light III, to obtain a cured product of the resin. The surface of the cured product was ground with #3000 waterproof abrasive paper and then buffed with 3-μm diamond paste into a mirror-polished surface. A 10-mm-square area in the center of the polished surface was roughened by means of carborundum. Each of the primer compositions of Examples and Comparative Examples was applied to such a roughened surface, and was dried by blowing air over the surface of the applied primer until the primer lost its flowability. Subsequently, each of the dental color tone adjustment compositions of Examples and Comparative Examples was applied and polymerized by irradiating it with light for 180 seconds using an irradiator for dental technology, α-light III (manufactured by Morita Corporation). A slurry containing 40 weight % of a toothpaste (manufactured by Lion Corporation under the trade name "White & White") and 60 weight % of distilled water was prepared. Bristles of a toothbrush (manufactured by Lion Corporation under the trade name "Between", Hardness of bristles: Regular) were brought into direct contact with the surface of the outermost layer of the specimen placed in the slurry, and the toothbrush was slid back and forth 40,000 times with an amplitude of 10 cm under a load of 250 g. Afterwards, the gloss of the surface was measured using a gloss meter ("VG 2000" manufactured by NIPPON DENSHOKU INDUSTRIES CO., LTD.) and expressed as a ratio (gloss value) to the gloss of a mirror defined as 100%. The angle selected for the measurement was 60 degrees. The gloss value (gloss retention) was preferably 40% or more, more preferably 45% or more, and even more preferably 55% or more.

[Method for Measuring Viscosity]

An amount of 0.6 cc of each of the dental color tone adjustment compositions of Examples and Comparative Examples was sampled, and measured for its viscosity at 23° C. using an E-type viscometer (VISCONIC ED, manufactured by TOKYO KEIKI INC.).

[Color Imparting Properties]

A mold having dimensions of 15 mm (diameter)×1 mm was filled with a hard resin for tooth crowns, ESTENIA C&B (E4, manufactured by Kuraray Noritake Dental Inc.), which was polymerized into a cured sheet by irradiating it with light for 180 seconds using an irradiator for dental technology, a-light III (manufactured by Morita Corporation). The color tone was measured for the cured sheet, which was defined as a "chromaticity measurement sheet 1". Each of the primer compositions of Examples and Comparative Examples was applied to such a chromaticity measurement sheet 1 and was dried by blowing air over the surface of the applied primer until the primer lost its flowability. Subsequently, each of the dental color tone adjustment compositions of Examples and Comparative Examples was applied to a thickness of 50 μm, and was polymerized by irradiating it with light for 180 seconds using an irradiator for dental technology, α-light III (manufactured by Morita Corporation). The resulting cured product was defined as a "chromaticity measurement sheet 2". The chromatic parameters (Lab) of the chromaticity measurement sheets 1 and 2 as test specimens were measured using a color-difference meter ("SE 6000", manufactured by NIPPON DENSHOKU INDUSTRIES CO., LTD.) and using illuminant D65/2 as a light source, with a standard white plate being placed behind the test specimens. Chromaticity measurement sheets were further fabricated and measured for the chromatic parameters in the same manner as above, except that each of the dental color tone adjustment compositions of Examples and Comparative Examples was applied to a thickness of 80 μm or 130 μm. The chromatic parameters of the chromaticity measurement sheet 1 were expressed as $L_1$, $a_1$, and $b_1$. The chromatic parameters of the chromaticity measurement sheet 2 were expressed as $L_2$, $a_2$, and $b_2$. The color difference (ΔE) was calculated according to the following equation.

$$\Delta E = ((L_1-L_2)^2+(a_1-a_2)^2+(b_1-b_2)^2)^{0.5}$$

There was calculated the slope of a linear regression line drawn using the values of the thicknesses of the applied color tone adjustment materials as X values and the values of ΔE as Y values. The slope is preferably 0.1 or less and more than 0.

[Test for Sedimentation]

An amount of 40 ml of each of the dental color tone adjustment compositions of Examples and Comparative Examples was put in a 50 ml screw cap bottle (manufactured by AS ONE Corporation) and then vigorously stirred with a static mixer for 30 seconds. Afterwards, the composition was allowed to stand for 1 hour. This was followed by visual check for the presence or absence of a sediment at the bottom of the container. The rating "Poor" was given when a sediment was observed, while the rating "Good" was given when no sedimentation was observed.

TABLE 1

| Parts by weight | | | Example 1 | Example 2 | Example 3 | Example 4 | Example 5 | Example 6 | Example 7 | Comp. Example 1 | Comp. Example 2 | Comp. Example 3 |
|---|---|---|---|---|---|---|---|---|---|---|---|---|
| Primer composition No. | | | 1 | 2 | 3 | 4 | 5 | 6 | 7 | 8 | 9 | 10 |
| A | a | MDP | 3 | 0.1 | 30 | 40 | — | 3 | 3 | — | 50 | 0.01 |
| | | M12P | — | — | — | — | 3 | — | — | — | — | — |
| | b | EtOH | 97 | 99.9 | 70 | 60 | 97 | — | — | — | 50 | 99.99 |
| | | MMA | — | — | — | — | — | 97 | — | — | — | — |
| | | Acetone | — | — | — | — | — | — | 97 | — | — | — |
| Color tone adjustment composition No. | | | 1 | 1 | 1 | 1 | 1 | 1 | 1 | 1 | 1 | 1 |
| B | d1 | DPE-6A | 50 | 50 | 50 | 50 | 50 | 50 | 50 | 50 | 50 | 50 |
| | d2 | MMA | 40 | 40 | 40 | 40 | 40 | 40 | 40 | 40 | 40 | 40 |
| | f | R972 | 10 | 10 | 10 | 10 | 10 | 10 | 10 | 10 | 10 | 10 |
| | e | TMDPO | 3 | 3 | 3 | 3 | 3 | 3 | 3 | 3 | 3 | 3 |
| | h | Yellow pigment | 0.09 | 0.09 | 0.09 | 0.09 | 0.09 | 0.09 | 0.09 | 0.09 | 0.09 | 0.09 |
| | | Red pigment | 0.01 | 0.01 | 0.01 | 0.01 | 0.01 | 0.01 | 0.01 | 0.01 | 0.01 | 0.01 |
| | | Black pigment | 0.1 | 0.1 | 0.1 | 0.1 | 0.1 | 0.1 | 0.1 | 0.1 | 0.1 | 0.1 |
| | g | Titanium dioxide | 0.6 | 0.6 | 0.6 | 0.6 | 0.6 | 0.6 | 0.6 | 0.6 | 0.6 | 0.6 |
| Surface-drying characteristics | | | Good | Good | Good | Good | Good | Good | Good | Good | Poor | Good |
| Bond strength (MPa) | | | 17 | 7 | 18 | 21 | 15 | 7 | 18 | 0.3 | 18 | 1.2 |
| After coffee staining treatment | ΔE* | | 3 | 4 | 3 | 5 | 3 | 4 | 3 | 6.1 | 7 | 6 |
| After abrasion treatment | ΔE* | | 2 | 2 | 2 | 2 | 2 | 2 | 2 | 10 | 2 | 10 |

TABLE 2

| Parts by weight | | | Example 8 | Example 9 | Example 10 | Example 11 | Example 12 | Example 13 | Example 14 | Example 15 | Example 16 | Example 17 | Comp. Example 4 | Comp. Example 5 | Comp. Example 6 |
|---|---|---|---|---|---|---|---|---|---|---|---|---|---|---|---|
| Primer composition No. | | | 11 | 12 | 13 | 14 | 15 | 16 | 17 | 18 | 19 | 20 | 21 | 22 | 23 |
| A | a | MDP | 0.05 | 1 | 39 | 5 | 5 | — | 1 | 1 | 1 | 1 | — | 5 | 0.01 |
| | | M12P | — | — | — | — | — | 1 | — | — | — | — | — | — | — |
| | b | EtOH | 99.9 | 94 | 60 | 70 | 60 | 94 | 94 | 94 | — | — | 97 | 50 | 99.98 |
| | | MMA | — | — | — | — | — | — | — | — | 94 | — | — | — | — |
| | | Acetone | — | — | — | — | — | — | — | — | — | 94 | — | — | — |
| | c | KBM 503 | 0.05 | 5 | 1 | 25 | 35 | 5 | — | — | 5 | 5 | 3 | 45 | 0.01 |
| | | KBE 903 | — | — | — | — | — | — | 5 | — | — | — | — | — | — |
| | | 11-MUS | — | — | — | — | — | — | — | 5 | — | — | — | — | — |
| Color tone adjustment composition No. | | | 1 | 1 | 1 | 1 | 1 | 1 | 1 | 1 | 1 | 1 | 1 | 1 | 1 |
| Surface-drying characteristics | | | Good | Good | Good | Good | Good | Good | Good | Good | Good | Good | Good | Poor | Good |
| Bond strength (MPa) | | | 9 | 23 | 8 | 16 | 11 | 10 | 15 | 18 | 9 | 18 | 0.3 | 11 | 0.2 |
| After coffee staining treatment | ΔE* | | 3.9 | 2.5 | 4 | 3.2 | 4.3 | 4.1 | 4.2 | 3.8 | 3.3 | 2.8 | 6.9 | 4 | 6.7 |
| After abrasion treatment | ΔE* | | 2 | 2 | 2 | 2 | 2 | 2 | 2 | 2 | 2 | 2 | 10 | 2 | 10 |

TABLE 3

| Parts by weight | | | Example 18 | Example 19 | Example 20 | Example 21 | Example 22 | Example 23 | Example 24 | Example 25 |
|---|---|---|---|---|---|---|---|---|---|---|
| Primer composition No. | | | 1 | 1 | 1 | 1 | 1 | 1 | 1 | 1 |
| Color tone adjustment composition No. | | | 1 | 2 | 3 | 4 | 5 | 6 | 7 | 8 |
| B | d1 | DPE-6A | 50 | — | 50 | 52 | 47 | 50 | 50 | 50 |
| | | PE-3A | — | 50 | — | — | — | — | — | — |
| | d2 | MMA | 40 | 40 | — | 42 | 38 | 40 | 40 | 40 |
| | | EMA | — | — | 40 | — | — | — | — | — |
| | d3 | UDMA | — | — | — | — | — | — | — | — |
| | | U-4TH | — | — | — | — | — | — | — | — |
| | | 3G | — | — | — | — | — | — | — | — |
| | e | TMDPO | 3 | 3 | 3 | 3 | 3 | 3 | 3 | 3 |
| | | CQ | 1 | — | — | — | — | — | — | — |
| | | Amine | — | — | — | — | — | — | — | — |
| | f | R972 | 10 | 10 | 10 | 6 | 15 | 10 | 10 | 10 |
| | | Ar380 | — | — | — | — | — | — | — | — |
| | | OX50 | — | — | — | — | — | — | — | — |
| | | AL-C | — | — | — | — | — | — | — | — |
| | g | Titanium dioxide | 0.6 | 0.6 | 0.6 | 0.6 | 0.6 | 0.05 | 1 | 1.8 |
| | h | Yellow pigment | 0.09 | 0.09 | 0.09 | 0.09 | 0.09 | 0.09 | 0.09 | 0.09 |
| | | Red pigment | 0.01 | 0.01 | 0.01 | 0.01 | 0.01 | 0.01 | 0.01 | 0.01 |
| | | Black pigment | 0.1 | 0.1 | 0.1 | 0.1 | 0.1 | 0.1 | 0.1 | 0.1 |
| Surface-drying characteristics | | | Good | Good | Good | Good | Good | Good | Good | Good |
| Gloss retention | | | 60 | 55 | 60 | 50 | 60 | 60 | 60 | 55 |
| After coffee staining treatment | ΔE* | | 3 | 3 | 3 | 4 | 3 | 4 | 4 | 3 |
| After abrasion treatment | ΔE* | | 2 | 2 | 2 | 2 | 2 | 2 | 2 | 2 |
| Viscosity of color tone adjustment material | mPa·s | | 43 | 33 | 42 | 28 | 67 | 43 | 42 | 42 |
| Test for pigment sedimentation | | | Good | Good | Good | Good | Good | Good | Good | Good |

TABLE 3-continued

| Parts by weight | | | Example 26 | Example 27 | Example 28 | Example 29 | Example 30 | Example 31 | Example 32 |
|---|---|---|---|---|---|---|---|---|---|
| Primer composition No. | | | 1 | 1 | 1 | 1 | 1 | 1 | 1 |
| Color tone adjustment composition No. | | | 9 | 10 | 11 | 12 | 13 | 12 | 13 |
| B | d1 | DPE-6A | 55 | 50 | 50 | 50 | 40 | 45 | 49 |
| | | PE-3A | — | — | — | — | — | — | — |
| | d2 | MMA | 40 | 40 | 40 | 40 | 40 | 40 | 40 |
| | | EMA | — | — | — | — | — | — | — |
| | d3 | UDMA | — | — | — | — | — | — | — |
| | | U-4TH | — | — | — | — | 10 | 5 | 1 |
| | | 3G | — | — | — | — | — | — | — |
| | e | TMDPO | 3 | 3 | 3 | — | 3 | 3 | 3 |
| | | CQ | — | — | — | 1 | — | — | — |
| | | Amine | — | — | — | 0.5 | — | — | — |
| | f | R972 | — | — | — | 10 | 10 | 10 | 10 |
| | | Ar380 | 5 | — | — | — | — | — | — |
| | | OX50 | — | 10 | — | — | — | — | — |
| | | AL-C | — | — | 10 | — | — | — | — |
| | g | Titanium dioxide | 0.6 | 0.6 | 0.6 | 0.6 | 0.6 | 0.6 | 0.6 |
| | h | Yellow pigment | 0.09 | 0.09 | 0.09 | 0.09 | 0.09 | 0.09 | 0.09 |
| | | Red pigment | 0.01 | 0.01 | 0.01 | 0.01 | 0.01 | 0.01 | 0.01 |
| | | Black pigment | 0.1 | 0.1 | 0.1 | 0.1 | 0.1 | 0.1 | 0.1 |
| Surface-drying characteristics | | | Good | Good | Good | Good | Average | Good | Average |
| Gloss retention | | | 50 | 60 | 60 | 60 | 50 | 55 | 60 |
| After coffee staining treatment | ΔE* | | 3 | 4 | 3 | 3 | 4 | 3 | 3 |
| After abrasion treatment | ΔE* | | 2 | 2 | 2 | 2 | 2 | 2 | 2 |
| Viscosity of color tone adjustment material | mPa · s | | 53 | 32 | 63 | 43 | 45 | 43 | 44 |
| Test for pigment sedimentation | | | Good | Good | Good | Good | Good | Good | Good |

TABLE 4

| Parts by weight | | | Comp. Example 7 | Comp. Example 8 | Comp. Example 9 | Comp. Example 10 | Comp. Example 11 | Comp. Example 12 | Comp. Example 13 | Comp. Example 14 | Comp. Example 15 |
|---|---|---|---|---|---|---|---|---|---|---|---|
| Primer composition No. | | | 1 | 1 | 1 | 1 | 1 | 1 | 1 | 1 | 1 |
| Color tone adjustment composition No. | | | 14 | 15 | 16 | 17 | 18 | 19 | 20 | 21 | 22 |
| B | d1 | DPE-6A | — | 50 | — | 50 | 57 | 35 | 50 | 50 | 50 |
| | | PE-3A | — | — | — | — | — | — | — | — | — |
| | d2 | MMA | — | — | 50 | 40 | 40 | 40 | 40 | 40 | 40 |
| | | EMA | — | — | — | — | — | — | — | — | — |
| | d3 | UDMA | 50 | 15 | 15 | — | — | — | — | — | — |
| | | U-4TH | 20 | 15 | 15 | — | — | — | — | — | — |
| | | 3G | 20 | 10 | 10 | — | — | — | — | — | — |
| | e | TMDPO | 3 | 3 | 3 | 3 | 3 | 3 | 3 | 3 | 3 |
| | | CQ | — | — | — | — | — | — | — | — | — |
| | | Amine | — | — | — | — | — | — | — | — | — |
| | f | R972 | 10 | 10 | 10 | — | 3 | 25 | 10 | 10 | — |
| | | Ar380 | — | — | — | — | — | — | — | — | — |
| | | OX50 | — | — | — | — | — | — | — | — | — |
| | | AL-C | — | — | — | — | — | — | — | — | — |
| | f' | NF180 | — | — | — | 10 | — | — | — | — | — |
| | | Monodisperse | — | — | — | — | — | — | — | — | 10 |
| | g | Titanium dioxide | 0.6 | 0.6 | 0.6 | 0.6 | 0.6 | 0.6 | 0.6 | 0.03 | 0.6 |
| | h | Yellow pigment | 0.09 | 0.09 | 0.09 | 0.09 | 0.09 | 0.09 | — | 0.09 | 0.09 |
| | | Red pigment | 0.01 | 0.01 | 0.01 | 0.01 | 0.01 | 0.01 | — | 0.01 | 0.01 |
| | | Black pigment | 0.1 | 0.1 | 0.1 | 0.1 | 0.1 | 0.1 | — | 0.1 | 0.1 |
| Surface-drying characteristics | | | Poor | Poor | Poor | Good | Good | Good | Good | Good | Good |
| Gloss retention | | | 50 | 50 | 50 | 40 | 50 | 60 | 60 | 60 | 50 |
| After coffee staining treatment | ΔE* | | 3 | 3 | 3 | 4 | 3 | 4 | 4 | 4 | 3 |
| After abrasion treatment | ΔE* | | 2 | 2 | 2 | 7 | 3 | 3 | 3 | 3 | 2 |

TABLE 4-continued

| Parts by weight | | Comp. Example 7 | Comp. Example 8 | Comp. Example 9 | Comp. Example 10 | Comp. Example 11 | Comp. Example 12 | Comp. Example 13 | Comp. Example 14 | Comp. Example 15 |
|---|---|---|---|---|---|---|---|---|---|---|
| Viscosity of color tone adjustment material | mPa·s | 5000 | 10000 | 10 | 19 | 15 | 570 | 33 | 43 | 10 |
| Test for pigment sedimentation | | Good | Good | Poor | Good | Poor | Good | Good | Good | Poor |

TABLE 5

| | Parts by weight | Example 33 | Example 34 | Example 35 | Comp. Example 16 | Comp. Example 17 | Comp. Example 18 |
|---|---|---|---|---|---|---|---|
| | Primer composition No. | 1 | 1 | 1 | 1 | 1 | 1 |
| | Color tone adjustment composition No. | 6 | 1 | 7 | 21 | 23 | 20 |
| B | d1  DPE-6A | 50 | 50 | 50 | 50 | 50 | 50 |
| | d2  MMA | 40 | 40 | 40 | 40 | 40 | 40 |
| | e   TMDPO | 3 | 3 | 3 | 3 | 3 | 3 |
| | f   R972 | 10 | 10 | 10 | 10 | 10 | 10 |
| | Monodisperse | — | — | — | — | — | — |
| | g   Titanium dioxide | 0.05 | 0.6 | 1 | 0.03 | — | 0.6 |
| | h   Yellow pigment | 0.09 | 0.09 | 0.09 | 0.09 | 0.09 | — |
| | Red pigment | 0.01 | 0.01 | 0.01 | 0.01 | 0.01 | — |
| | Black pigment | 0.1 | 0.1 | 0.1 | 0.1 | 0.1 | — |
| | 50 μm ΔE | 15 | 17.5 | 19.3 | 10.9 | 5.2 | 3.6 |
| | 80 μm ΔE | 20.5 | 18.6 | 20.7 | 15.6 | 12.6 | 5.8 |
| | 130 μm ΔE | 23 | 24.1 | 25.5 | 24.9 | 25.5 | 7.2 |
| | Slope | 0.095 | 0.085 | 0.079 | 0.176 | 0.254 | 0.043 |

In Comparative Example 18, the values of ΔE measured in the test for color imparting properties were not more than 10 for all of the thicknesses of 50 μm, 80 μm, and 130 μm. The too small values of ΔE indicate the failure to achieve sufficient color impartation in Comparative Example 18.

INDUSTRIAL APPLICABILITY

The dental color tone adjustment material kit of the present invention is adapted to show good surface-drying characteristics, enable good bonding to adherends (dental restorative materials, in particular), reduce the susceptibility of the cure product of the dental color tone adjustment material to discoloration by a substance such as coffee after curing, exhibit improved abrasion resistance, achieve sufficient color impartation, and allow adjustment to a desired color tone to be made even by applying the material thinly. The dental color tone adjustment material kit of the present invention undergoes no sedimentation of the pigment and is thus free of defects such as color unevenness.

The invention claimed is:

1. A dental color tone adjustment material kit, comprising a primer composition (A) and a dental color tone adjustment material (B), wherein
   the primer composition (A) comprises an acid group-containing polymerizable monomer (a) and a volatile organic solvent (b),
   the dental color tone adjustment material (B) comprises a polymerizable monomer (d), a polymerization initiator (e), particle aggregates (f), titanium dioxide (g), and a pigment (h),
   a content of the acid group-containing polymerizable monomer (a) is 0.05 to 45 weight % of a total weight of the primer composition (A),
   a content of the volatile organic solvent (b) is 55 to 99.95 weight % of a total weight of the primer composition (A),
   the polymerizable monomer (d) comprises a polyfunctional acrylate monomer (d1) having three or more acryloyl groups per molecule and a volatile monofunctional (meth)acrylate monomer (d2),
   a total content of the monomer (d1) and the monomer (d2) is 88 weight % or more of a weight of the polymerizable monomer (d),
   the particle aggregates (f) are chain aggregates of ultrafine filler particles having an average primary particle diameter of 1 to 50 nm,
   a content of the particle aggregates (f) is 5 to 20 parts by weight per 100 parts by weight of a total weight of the polymerizable monomer (d) and the particle aggregates (f),
   a content of the titanium dioxide (g) is 0.05 to 2 parts by weight per 100 parts by weight of a total weight of the polymerizable monomer (d) and the particle aggregates (f), and
   the pigment (h) is a pigment other than the titanium dioxide (g).

2. The dental color tone adjustment material kit according to claim 1, wherein the primer composition (A) further comprises a silane coupling agent (c) and has the following composition:
   0.05 to 40 weight % of the acid group-containing polymerizable monomer (a);
   55 to 99.9 weight % of the volatile organic solvent (b); and
   0.01 to 40 weight % of the silane coupling agent (c).

3. The dental color tone adjustment material kit according to claim 1, wherein the primer composition (A) is free of water.

4. The dental color tone adjustment material kit according to claim 1, wherein the dental color tone adjustment material (B) has a viscosity of 20 to 500 mPa·s at 23° C.

5. A color tone adjustment material kit for dental restorative materials, the color tone adjustment material kit comprising the dental color tone adjustment material kit according to claim 1.

* * * * *